US007208507B2

(12) United States Patent
Hong et al.

(10) Patent No.: US 7,208,507 B2
(45) Date of Patent: Apr. 24, 2007

(54) PYRIDINES AND USES THEREOF

(75) Inventors: Feng Hong, Seattle, WA (US); J Peter Klein, Vashon, WA (US)

(73) Assignee: Cell Therapeutics, Inc., Seattle, WA (US)

( * ) Notice: Subject to any disclaimer, the term of this patent is extended or adjusted under 35 U.S.C. 154(b) by 1 day.

(21) Appl. No.: 11/056,777

(22) Filed: Feb. 11, 2005

(65) Prior Publication Data

US 2005/0182102 A1 Aug. 18, 2005

Related U.S. Application Data

(63) Continuation of application No. 10/667,916, filed on Sep. 22, 2003, now Pat. No. 6,875,781.

(60) Provisional application No. 60/460,782, filed on Apr. 4, 2003.

(51) Int. Cl.
*A61K 31/44* (2006.01)
*C07D 213/72* (2006.01)

(52) U.S. Cl. .................. 514/352; 546/312; 546/307; 546/304; 546/290; 514/345

(58) Field of Classification Search .............. 514/352, 514/345; 546/312, 307, 304, 290
See application file for complete search history.

(56) References Cited

U.S. PATENT DOCUMENTS

| | | | |
|---|---|---|---|
| 3,119,823 A | 1/1964 | Shapiro | 260/249.9 |
| 3,933,814 A | 1/1976 | Haberkorn et al. | 260/248 NS |
| 3,948,893 A | 4/1976 | Aichinger et al. | 260/248 NS |
| 3,966,725 A | 6/1976 | Reisdorff et al. | 260/248 NS |
| 4,219,552 A | 8/1980 | Haberkorn et al. | 424/249 |
| 4,499,269 A | 2/1985 | Bennion et al. | 544/198 |
| 5,102,927 A | 4/1992 | Rody et al. | 524/100 |
| 5,260,362 A | 11/1993 | Rody et al. | 524/100 |
| 5,545,836 A | 8/1996 | Reinehr et al. | 544/216 |
| 5,702,717 A | 12/1997 | Cha et al. | 424/425 |
| 5,856,331 A | 1/1999 | Bursten et al. | 514/263 |
| 6,004,985 A | 12/1999 | Kochanny et al. | 514/341 |
| 6,150,360 A | 11/2000 | Daeyaert et al. | 514/236.2 |
| 6,150,362 A | 11/2000 | Henkin et al. | 514/245 |
| 6,150,382 A | 11/2000 | Kochanny et al. | 514/341 |
| 6,166,014 A | 12/2000 | Kochanny et al. | 514/241 |
| 6,193,960 B1 | 2/2001 | Metzger et al. | 424/59 |
| 6,288,228 B1 | 9/2001 | Henkin et al. | 544/197 |

FOREIGN PATENT DOCUMENTS

| | | |
|---|---|---|
| DE | 1200314 | 9/1965 |
| DE | 2226474 | 2/1973 |
| EP | 525 262 A1 | 2/1993 |
| FR | 1321624 | 3/1963 |
| JP | 48-28486 | 4/1973 |
| JP | 49-69688 | 7/1974 |
| SU | 274102 | 4/1970 |
| WO | WO 91/11465 | 8/1991 |
| WO | WO 00/25780 | 5/2000 |
| WO | WO 01/25220 | 4/2001 |
| WO | WO 02/22584 | * 3/2002 |
| WO | WO 02/36578 | 5/2002 |

OTHER PUBLICATIONS

Butler, D.E. et al.: Novel pharmacological activity of a series of substituted pyridines. J. Med. Chem. vol. 14, pp. 575-579, 1971.*
Compounds with RN 417724-78-8 and 417721-23-4, published in WO 02/32872, Apr. 25, 2002.*
Anonymous, "Inhibiting LPAAT-β slows tumor growth in animal models," *Hematological Oncology Today*, Feb. 3, 2003, p. 45.
Britten and Kohne, "Repeated Sequences in DNA," *Science 161* (3841): 529-540, Aug. 9, 1968.
Brodskii et al., "The mechanism underlying the action of secondary aromatic amine- type antioxidants and their ethers on the radiation oxidation of N-butylpropionamide and polycaproamide," *Chemical Abstracts*, Accession No. 69:3284, 1968.
Budesinsky et al., "Substituted 2, 4-diamino-6-phenyl-1,3,5-triazines," *Chemical Abstracts*, Accession No. 97:6328, 1982.
Burmistrov et al., "6-Amino-4-arylamino-2-(o-hydroxyphenyl) triazines," *Chemical Abstracts*, Accession No. 61:47941, 1964.
Burnsten et al., "Interleukin-1 Rapidly Stimulates Lysophosphatidate Acyltransferase and Phosphatidate Phosphohydrolase Activities in Human Mesangial Cells," *Journal of Biological Chemistry 266*(31): 20732-20743, Nov. 5, 1991.
Bursten et al., "Lipid A activation of glomerular mesangial cells: mimicry of the bioactive lipid, phosphatidic acid," *American Journal of Physiology 262*(2): C328-C338, Feb. 1992.
Chen, C. et al., "A Convenient Synthetic Method for Trisubstituted s-Triazines," *Chemical Abstracts*, Accession No. 124:146076, 1995.
Compounds with RN 545396-39-2, RN 34891-38-8 and RN 19933-09-6.
Eberhardt et al., "Human Lysophosphatidic Acid Acyltransferase," *Journal of Biological Chemistry 272*(32): 20299-20305, Aug. 8, 1997.
Elkafrawy, A.F. et al., "Synthesis and reactions of some 4-aryl-2-benzylthio-1, 6-dihydro-6-thiono-1,3,5-triazines," *Chemical Abstracts*, Accession No. 115:279963, 1991.
English, D., "Phosphatidic acid: A lipid messenger involved in intracellular and extracellular signaling," *Cell Signal 8*(5): 341-347, 1996.
Fong and Engleman, "Dendritic Cells in Cancer Immunotherapy," *Annual Review of Immunology 18*: 245-273, 2000.
Fusco, R. et al., "Reaction of arylazochloroacetic esters with tertiary cyclic bases," *Gazzetta Chimica Italiana 98*(5): 511-534, 1968. English Translation.
Haviv, F. et al., "2-[(Phenylthio)methyl]pyridine Derivaties: New Antiinflamatory Agents," *J. Med. Chem. 26*: 218-222, 1983.
Hoess and Abremski, "The Cre-lox Recombination System," *Nucleic Acids and Molecular Biology 4*: 99-109, 1990.
Imamura et al, "Induction of *in vitro* tumor cell invasion of cellular monolayers by lysophosphatidic acid or phospholipase D," *Biochemical and Biophysical Research Communications 193*(2): 497-503, Jun. 15, 1993.

(Continued)

*Primary Examiner*—Charanjit S. Aulakh
(74) *Attorney, Agent, or Firm*—Seed IP Law Group PLLC

(57) ABSTRACT

The invention relates to pyridines and uses thereof, including to inhibit lysophosphatidic acid acyltransferase β (LPAAT-β) activity and/or proliferation of cells such as tumor cells.

16 Claims, No Drawings

OTHER PUBLICATIONS

Kester, M., "Platelet-Activating Factor Stimulates Phosphatidic Acid Formation in Culture Rat Mesangial Cells: Roles of Phospholipase D, Diglyceride Kinase, and De Novo Phospholipid Synthesis," *Journal of Cellular Physiology 156* : 317-325, 1993.

Köhler and Milstein, "Continuous cultures of fused cells secreting antibody of predefined specificity," *Nature 256*: 495-497, Aug. 7, 1975.

Kume and Shimizu, "cDNA Cloning and Expression of Murine 1-Acyl-sn-glycerol-3-phosphate Acyltransferase," *Biochemical and Biophysical Research Communications 237*(3): 663-666, Aug. 28, 1997.

Leung et al., "Molecular Cloning of Two Alternatively Spliced Forms of Human Phosphatidic Acid Phosphatase cDNAs that Are Differentially Expressed in Normal and Tumor Cells," *DNA and Cell Biology 17*(4): 377-385, Apr. 1998.

Losman et al., "Baboon anti-idiotype antibodies mimic a carcinoembryonic antigen epitope," *Int. J. Cancer 46*(2): 310-314, Aug. 15, 1990.

Martin et al., "Increased concentrations of phosphatidate, diacylglycerol and ceramide in ras- and tyrosine kinase (fps)-transformed fibroblasts," *Oncogene 14*(13):1571-1580, Apr. 3, 1997.

Michalik, M. et al., "Synthesis of nitrogen-containing heterocycles," *Chemical Abstracts*, Accession No. 79:18680, 1973.

Miller and Rosman, "Improved Retroviral Vectors for Gene Transfer and Expression," *BioTechniques 7*(9): 980-EOA, Oct. 1989.

Moolenaar, W.H., "Lysophosphatidic Acid, a Multifunctional Phospholipid Messenger," *Journal of Biological Chemistry 270*(22): 12949-12952, Jun. 2, 1995.

Moussa, G.E.M. et al., "Some reactions on 4-aryl-2-substituted amino-1,6-dihydro-6-thioxo-1,3,5 triazines," *Chemical Abstracts*, Accession No. 113:59112, 1990.

Orlandi et al., "Cloning immunoglobulin variable domains for expression by the polymerase chain reaction," *Proc. Natl. Acad. Sci. USA 86*(10): 3833-3837, May 1989.

Pitts et al., "Rapid Synthesis of Triazine Inhibitors of Inosine Monophoshate Dehydrogenase," *Bioorganic & Medicinal Chemistry Letters 12*: 2137-2140; 2002.

Prostakov, N.S. et al., "Substituted Pyridines. 5-Methyl-4-Phenyl-2-(Aminoalkoxy, Aroxymethyl)pyridines," *Chemistry of Heterocyclic Compounds 7*(9): 1137-1138, Sep. 1971.

Rizzo et al., "The Recruitment of Raf-1 to Membranes Is Mediated by Direct Interaction with Phosphatidic Acid and Is Independent of Association with Ras," *Journal of Biological Chemistry 275*(31): 23911-23918, Aug. 4, 2000.

Sauer, B., "Inducible Gene Targeting in Mice Using the Cre/lox System," *Methods: A Companion to Methods in Enzymology 14*(4): 381-392, Apr. 1998.

Schreurs et al., "Dendritic Cell-Based Vaccines: From Mouse Models to Clinical Cancer Immunotherapy," *Critical Reviews in Oncogenesis 11*(1): 1-17, 2000.

Shapiro, S.L. et al., "Guanamines. VIII. 6-(Substituted-phenyl) guanamines," *Chemical Abstracts*, Accession No. 56:60602, 1962.

Sharp et al., "Viral DNA in Transformed Cells. I.A Study of the Sequences of Adenovirus 2 DNA in a Line of Transformed Rat Cells Using Specific Fragments of the Viral Genome," *J. Mol. Biol. 86*(4): 709-726, Jul. 15, 1974.

Sluka et al., "2,4-diamino-6-phenyl-1,3,5-triazines," *Collection Czechoslov. Chem. Commun. 43*: 1639-1646, 1978.

Stamps et al., "A human cDNA sequence with homology to non-mammalian lysophosphatidic acid acyltransferases," *Biochemical Journal 326*:455-461, Sep. 1, 1997.

Sutton, W.D., "A crude nuclease preparation suitable for use in DNA reassociation experiments," *Biochimica et Biophysica Acta 240*(4): 522-531, Jul. 29, 1971.

West et al., "Cloning and Expression of Two Human Lysophosphatidic Acid Acyltransferase cDNAs That Enhance Cytokine-Induced Signaling Responses in Cells," *DNA and Cell Biology 16* (6): 691-701, Jun. 1997.

Wetmur and Davidson, "Kinetics of Renaturation of DNA," *Journal of Molecular Biology 31*(3): 349-370, Feb. 14, 1968.

Xu et al, "Lysophospholipids activate ovarian and breast cancer cells," *Biochemical Journal 309*: 933-940, Aug. 1, 1995.

Yuki, Y. et al., "Preparation of amino-s-triazines with amino-or nitrophenyl groups," *Chemical Abstracts*, Accession No. 75:151765, 1971.

Zimmerman, J. et al., "Phenylamino-Pyrimidine (PAP) Derivatives: A New Class of Potent and Selective Inhibitors of Protein Kinase C (PKC)," *Arch. Pharm. Pharm. Med. Chem.329* :371-376, 1996.

\* cited by examiner

SEQUENCE LISTING

<160> NUMBER OF SEQ ID NOS: 3

<210> SEQ ID NO 1
<211> LENGTH: 39
<212> TYPE: DNA
<213> ORGANISM: Artificial Sequence
<220> FEATURE:
<223> OTHER INFORMATION: Primer

<400> SEQUENCE: 1
tgatatccga agaagatctt atggagctgt ggccgtgtc            39

<210> SEQ ID NO 2
<211> LENGTH: 29
<212> TYPE: DNA
<213> ORGANISM: Artificial Sequence
<220> FEATURE:
<223> OTHER INFORMATION: Primer

```
<400> SEQUENCE: 2
caggctctag actactgggc cggctgcac                                         29

<210> SEQ ID NO 3
<211> LENGTH: 42
<212> TYPE: DNA
<213> ORGANISM: Artificial Sequence
<220> FEATURE:
<223> OTHER INFORMATION: Primer

<400> SEQUENCE: 3
cctacgtcga catggaacaa aaattgatat ccgaagaaga tc                          42
```

PYRIDINES AND USES THEREOF

CROSS-REFERENCES TO RELATED APPLICATIONS

This application is a continuation of U.S. patent application Ser. No. 10/667,916, filed Sep. 22, 2003 and allowed Nov. 10, 2004; which application claims the benefit of U.S. Provisional Application No. 60/460,782, filed Apr. 4, 2003, which applications are incorperated by reference herein in their entirety.

BACKGROUND OF THE INVENTION

1. Field of the Invention

The invention is in the field of organic and medicinal chemistry. In particular, the invention relates to pyridines and uses thereof, such as inhibiting the activity of lysophosphatidic acid acyltransferase β (LPAAT-β) activity and/or inhibiting the proliferation of a cell (e.g., tumor cell).

2. Description of the Related Art

Lysophosphatidic acid acyltransferase (LPAAT) catalyzes the acylation of lysophosphatidic acid (LPA) to phosphatidic acid. LPA is the simplest glycerophospho-lipid, consisting of a glycerol molecule, a phosphate group, and a fatty acyl chain. LPAAT adds a second fatty acyl chain to LPA, producing phosphatidic acid (PA). PA is the precursor molecule for certain phosphoglycerides, such as phosphatidylinositol, and diacylglycerols, which are necessary for the production of other phosphoglycerides, such as phosphatidylcholine, and for triacylglycerols, which are essential biological fuel molecules.

In addition to being a crucial precursor molecule in biosynthetic reactions, LPA has been added to the list of intercellular lipid messenger molecules. LPA interacts with G protein-coupled receptors, coupling to various independent effector pathways including inhibition of adenylate cyclase, stimulation of phospholipase C, activation of MAP kinases, and activation of the small GTP-binding proteins Ras and Rho. Moolenaar, *J. Biol. Chem.* 28:1294 (1995). The physiological effects of LPA have not been fully characterized as yet. However, one of the physiological effects that is known is that LPA promotes the growth and invasion of tumor cells. It has been shown that the addition of LPA to ovarian or breast cancer cell lines induces cell proliferation, increases intracellular calcium levels, and activates MAP kinase. Xu et al., *Biochem. J.* 309:933 (1995). In addition, LPA has been shown to induce MM 1 tumor cells to invade cultured mesothelial cell monolayers. Imamura et al., *Biochem. Biophys. Res. Comm.* 193:497 (1993).

Like LPA, PA is also a messenger molecule. PA is a key messenger in a common signaling pathway activated by proinflammatory mediators such as interleukin-1β, tumor necrosis factor α, platelet activating factor, and lipid A. Bursten et al., *Am. J. Physiol.* 262:C328 (1992); Bursten et al., *J. Biol. Chem.* 255:20732 (1991); Kester, *J. Cell Physiol.* 156:317 (1993). PA has been implicated in mitogenesis of several cell lines [English, Cell Signal 8:341 (1996)]. PA level has been found to be increased in either ras or fps transformed cell lines compared to the parental Rat2 fibroblast cell line [Martin et al., *Oncogene* 14:1571 (1997)]. Activation of Raf-1, an essential component of the MAPK signaling cascade, by extracellular signals is initiated by association with intracellular membranes. Recruitment of Raf-1 to membranes has been reported to be mediated by direct association with phosphatidic acid [Rizzo et al., *J. Biol. Chem.* 275:23911–8 (2000)]. Thus, LPAAT, as an enzyme that regulates PA content in cells, may play a role in cancer, and may also mediate inflammatory responses to various proinflammatory agents.

LPAAT exists in a LPAAT-α form and a LPAAT-β form. Northern blot analysis shows that LPAAT-α is expressed in all human tissues tested with the highest expression level found in skeletal muscle (West et al., *DNA Cell Biol.* 16:691 (1997)). The uniformity of LPAAT-α expression has also been found in additional tissues such as prostate, testis, ovary, small intestine, and colon (Stamps et al., *Biochem. J.* 326:455 (1997)) as well as in mouse tissues (Kume et al., *Biochem. Biophys. Res. Commun.* 237:663 (1997)). A 2 kb and a 1.3 kb forms, possibly due to alternative utilization of polyadenylation signals at the 3'-UTR, have been found in murine LPAAT-α mRNA (Kume et al., *Biochem. Biophys. Res. Commun* 237:663 (1997)), whereas only one major human LPAAT-α mRNA of 2 kb in size has been detected by Northern analysis. West et al., *DNA Cell Biol.* 16:691 (1997); Stamps et al., *Biochem. J.* 326:455 (1997).

In contrast, LPAAT-β demonstrates a distinct tissue distribution of mRNA expression. West et al., *DNA Cell Biol.* 16:691 (1997). LPAAT-β is most highly expressed in liver and heart tissues. LPAAT-β is also expressed at moderate levels in pancreas, lung, skeletal muscle, kidney, spleen, and bone marrow; and at low levels in thymus, brain and placenta. This differential pattern of LPAAT-β expression has been confirmed independently (Eberhardt et al., *J. Biol. Chem.* 272:20299 (1997)) with the only discrepancy being that high level, instead of moderate level, of LPAAT-β has been detected in pancreas, possibly due to slight lot variations in commercial RNA blots (Clontech, Palo Alto, Calif.). In addition, moderate LPAAT-β expression has been found in prostate, testis, ovary, small intestine, and colon with the small intestine containing relatively higher amounts. Eberhardt et al., *J. Biol. Chem.* 272:20299 (1997). Within various brain sections, high expression has been found in the subthalamic nucleus and spinal cord; and least in the cerebellum, caudate nucleus, corpus callosum, and hippocampus. LPAAT-β can also be detected in myeloid cell lines THP-1, HL-60, and U937 with the mRNA levels remaining the same with or without phorbal-ester treatment. The size difference between human LPAAT-α and LPAAT-β mRNA is consistent with the sequence data, in which LPAAT-α has a longer 3'-UTR. The differential tissue expression pattern LPAAT-α and LPAAT-β mRNA would suggest these two genes are regulated differently and are likely to have independent functions. Therefore, a desirable feature in compounds that inhibit LPAAT activity is that they are specific in inhibiting one isoform of the enzyme over the other (i.e., LPAAT-β over LPAAT-α).

LPAAT-β mRNA has been found to be elevated in tumor tissues (e.g., uterus, fallopian tube, and ovary), as compared to its expression in the corresponding normal tissues. However, no significant difference was found in LPAAT-α mRNA level between the various tumor tissues and the normal adjacent tissues. In two of the tumor tissues (fallopian tube and ovary) where LPAAT-α mRNA was elevated, PAP2-α mRNA expression was found to be suppressed, as it was also in tumors of the colon, rectum, and breast. Thus, LPAAT-β (rather than LPAAT-α) appears to be a relevant target for inhibition.

There is a need in the art for improved compositions and methods. The present invention fills this need, and further provides other related advantages.

BRIEF SUMMARY OF THE INVENTION

Briefly stated, the present invention provides a variety of compounds and uses thereof. More specifically, the compounds of the present invention are pyridines that possess aromatic substituents which are directly or indirectly attached to two non-adjacent carbons of the pyridine ring. The compounds are generally of the formula:

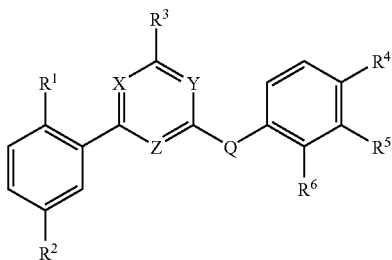

where $R^1$–$R^6$ are hydrogen or non-hydrogen substituents, Q is a heteroatom or heteroatom attached to one or more methylene groups, and one of X, Y and Z is N with the other two being CH or a substituted C. In preferred embodiments:

X, Y and Z are N, CH or CR where R is alkyl, alkoxy, Cl, Br, $NH_2$, NHR' or NR'R'' where R' and R'' independently are alkyl;

Q is NR, RN—$(CH_2)_n$, $(CH_2)_n$—NR, O, O—$(CH_2)_n$, $(CH_2)_n$—O, S, S—$(CH_2)_n$ or $(CH_2)_n$—S, where n is 1–10 and R is H or alkyl;

$R^1$ is H, OH, alkyl, alkoxy, Cl, F, Br, $CR_3$ where $R_3$ is $Cl_3$, $F_3$ or $Br_3$, $NH_2$, NHR or NRR' where R and R' independently are alkyl;

$R^2$ is H, OH, alkyl, alkoxy, Cl, F, Br or $CR_3$ where $R_3$ is $Cl_3$, $F_3$ or $Br_3$;

$R^3$ is H, alkyl, alkoxy, Cl, $CCl_3$, $NH_2$, NHR or NRR' where R and R' independently are alkyl or acyl;

$R^4$, $R^5$ and $R^6$ are independently H, OH, alkyl, alkenyl, alkynyl, alkoxy, $(CH_2)_n$—OR where R is H or alkyl and n is 1–10, Cl, F, Br, $CR_3$ where $R_3$ is $Cl_3$, $F_3$ or $Br_3$, acyl, heterocycle, $N^+(=O)O^-$, C≡N, $N_3$, SH, SR or $S(=O)_2R$ where R is alkyl, $NH_2$, NHR or NRR' where R and R' independently are alkyl, or $R^4$ and $R^5$ or $R^5$ and $R^6$ are taken together with the benzene ring to form a heterocycle;

and with the proviso that one of X, Y and Z is N.

A compound or salt thereof as described above may be combined with a pharmaceutical carrier or diluent to form a pharmaceutical composition of the present invention.

A compound, salt thereof or pharmaceutical composition of the present invention may be used in one or more methods. In one method, the activity of LPAAT-β may be reduced by the step comprising contacting LPAAT-β with a compound, salt thereof or pharmaceutical composition of the present invention in an amount effective to reduce LPAAT-β activity. In another method, the proliferation of a cell in which the activity of LPAAT-β is required for the proliferation of the cell may be inhibited by the step comprising contacting LPAAT-β with a compound, salt thereof or pharmaceutical composition of the present invention in an amount effective to inhibit the proliferation of the cell. In a further method, the treatment of a cancer in which LPAAT-β activity is associated may be effected by the step comprising administering to an animal in need a compound, salt thereof or pharmaceutical composition of the present invention in an amount effective to treat the cancer.

Also provided is a coated medical device for inhibiting the proliferation of a cell in which the activity of LPAAT-β is required for the proliferation of the cell comprising a medical device coated with a compound, salt thereof or pharmaceutical composition of the present invention.

These and other aspects of the present invention will become evident upon reference to the following detailed description.

DETAILED DESCRIPTION OF THE INVENTION

Prior to setting forth the invention, it may be helpful to an understanding thereof to set forth definitions of certain terms to be used hereinafter.

In the present description, the term "alkyl" refers to straight- or branched-chain hydrocarbons having from 1 to 10 carbon atoms and more preferably 1 to 8 carbon atoms which include, by way of example, methyl, ethyl, n-propyl, i-propyl, n-butyl, t-butyl and the like. The alkyl group may be substituted or unsubstituted. When substituted, the substituted group(s) is preferably one or more independently selected from alkyl, cycloalkyl, heteroalicyclic, aryl, heteroaryl, haloalkyl, halo, hydroxy, alkoxy, mercapto, cyano, sulfonamidyl, aminosulfonyl, acyl, acyloxy, substituted imino and substituted amino.

"Alkenyl" includes monovalent hydrocarbon radicals having straight, cyclic, or branched moieties, and combinations thereof which comprise at least one carbon-carbon double bond. The alkenyl group may be substituted or unsubstituted. When substituted, the substituted group(s) is preferably one or more independently selected from alkyl, acyl, cycloalkyl, heteroalicyclic, aryl, haloalkyl, alkoxy and substituted amino.

"Alkoxy" refers to the group "—O-alkyl" which includes, by way of example, methoxy, ethoxy, n-propoxy, i-propoxy, n-butoxy, t-butoxy and the like. It further refers to the group "—O-alkyl-W-alkyl" where W is O or N; for example, —O—$(CH_2)_n$—W—$(CH_2)_m$ where n and m are independently 1–10.

"Substituted amino" denotes the group —NRR, wherein each R group is independently selected from hydrogen, acyl, alkyl, cycloalkyl, aryl, or the R groups can be joined together with the nitrogen to form a heterocyclic ring (e.g., piperidine, piperazine, or a morpholine ring).

"Substituted imino" denotes the group =NR, wherein R is preferably selected from hydrogen, hydroxy, alkyl and acyl.

"Aryl" refers to an unsaturated aromatic carbocyclic group of 6 to 14 carbon atoms having a single ring (e.g., phenyl) or multiple condensed rings (e.g., naphthyl or anthryl). The aryl group may be unsubstituted or substituted; in the latter case, the substituent or substituents preferably are selected independently from alkyl, aryl, haloalkyl, halo, hydroxy, alkoxy, mercapto, cyano, sulfonamidyl, aminosulfonyl, acyl, acyloxy, nitro, and substituted amino.

"Heterocycle" includes "heteroaryl" and "heteroalicyclic". Examples of heterocycles include oxazole, piperidine, piperazine and morpholine.

"Heteroaryl" is a monocyclic or fused ring (i.e., rings which share an adjacent pair of atoms) group having in the ring(s) one or more atoms selected preferably from nitrogen, oxygen and sulfur and, in addition, having a completely conjugated p-electron system. Exemplary heteroaryl groups are pyrrole, furan, thiophene, imidazole, oxazole, thiazole, pyrazole, pyridine, pyrimidine, quinoline, isoquinoline, purine and carbazole. The heteroaryl group may be substituted or unsubstituted. When substituted, the substituted group(s) is preferably one or more independently selected from alkyl, aryl, haloalkyl, halo, hydroxy, alkoxy, mercapto, cyano, sulfonamidyl, aminosulfonyl, acyl, acyloxy, nitro and substituted amino.

"Cycloalkyl" encompasses cyclic alkyl groups that contain between 3 and 8 carbon atoms and have a single cyclic ring, illustrated by cyclopropyl, cyclobutyl, cyclopentyl, and cyclooctyl. The cycloalkyl ring may be substituted or unsubstituted. Again, a substituted cycloalkyl ring carries one or more substituent groups, independently selected preferably from alkyl, aryl, haloalkyl, halo, hydroxy, alkoxy, mercapto, cyano, sulfonamidyl, aminosulfonyl, acyl, acyloxy, vitro, and substituted amino.

"Heteroalicyclic" refers to a monocyclic or fused ring group having in the ring(s) one or more atoms selected preferably from nitrogen, oxygen and sulfur. The rings may also have one or more double bonds. However, the rings do not have a completely conjugated π-electron system. The heteroalicyclic ring may be substituted or unsubstituted. When substituted, the substituted group(s) preferably are selected independently from alkyl, aryl, haloalkyl, halo, hydroxy, alkoxy, mercapto, cyano, sulfonamidyl, aminosulfonyl, acyl, acyloxy, vitro, and substituted amino.

"Halogen" or "halo" refers to fluoro, chloro, bromo, iodo.

"Acyl" group refers to the C(O)—R" group, where R" is selected preferably from hydrogen, hydroxy, alkyl, haloalkyl, cycloalkyl, aryl optionally substituted with one or more alkyl, haloalkyl, alkoxy, halo and substituted amino groups, heteroaryl (bonded through a ring carbon) optionally substituted with one or more alkyl, haloalkyl, alkoxy, halo and substituted amino groups and heteroalicyclic (bonded through a ring carbon) optionally substituted with one or more alkyl, haloalkyl, alkoxy, halo and substituted amino groups. Acyl groups include aldehydes, ketones, acids, acid halides, esters and amides. Preferred acyl groups are carboxy groups, e.g., acids and esters. Esters include amino acid ester derivatives. The acyl group may be attached to a compound's backbone at either end of the acyl group, i.e., via the C or the R". Where the acyl group is attached via the R", then C will bear another substituent, such as hydrogen or alkyl.

The phrase "physiologically acceptable salt" refers to those salts that retain the biological effectiveness and properties of the particular compound. Physiologically acceptable salts are often useful because they may have improved stability and/or solubility in pharmaceutical compositions over the free base form of the compound. A physiologically acceptable salt may be obtained by reaction of a free base with an inorganic acid such as hydrochloric acid, hydrobromic acid, nitric acid, phosphoric acid, sulfuric acid, and perchloric acid and the like, or with an organic acid such as acetic acid, oxalic acid, malic acid, maleic acid, methanesulfonic acid, ethanesulfonic acid, p-toluenesulfonic acid, salicylic acid, tartaric acid, citric acid, succinic acid or malonic acid, and the like. A physiologically acceptable salt may also be obtained by reaction of a free acid with a base such as sodium, potassium or lithium hydroxide, bicarbonate or carbonate, and the like.

As noted above, the present invention provides pyridines, physiologically acceptable salts thereof and uses thereof. The pyridines possess aromatic substituents that are directly or indirectly attached to two non-adjacent carbons of the pyridine ring. The compounds are generally of the formula:

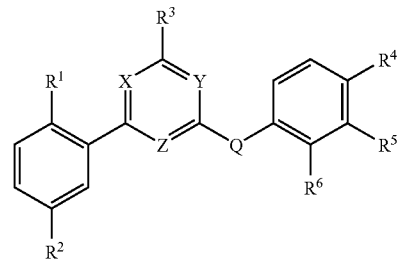

where $R^1$–$R^6$ are hydrogen or non-hydrogen substituents, Q is a heteroatom or heteroatom attached to one or more methylene groups, and two of X, Y and Z are N with the third being CH or a substituted C. The requirement that only one of X, Y and Z is N is consistent with the compounds including a pyridine ring.

Preferred embodiments include the following selections for the general formula above. Preferred embodiments include where X, Y and Z are N, CH or CR. R of CR is alkyl, alkoxy, halo (preferably Cl or Br), $NH_2$, NHR' or NR'R" where R' and R" independently are alkyl. Particularly preferred is where X or Y is N.

Preferred embodiments include where Q is a heteroatom (preferably N, O or S) and may be attached to one or more methylene groups to provide additional spacing between the pyridine ring and the phenyl ring possessing $R^4$, $R^5$ and/or $R^6$. Q may be NR where R is H or alkyl. Where there are one or more methylene groups, the heteroatom may be oriented such that it is attached directly to the pyridine ring or attached directly to the phenyl ring possessing $R^4$, $R^5$ and/or $R^6$. For example, Q may be RN—$(CH_2)_n$, $(CH_2)_n$—NR, O—$(CH_2)_n$, $(CH_2)_n$—O, S—$(CH_2)_n$ or $(CH_2)_n$—S, where n is typically 1–10 and R is H or alkyl. Particularly preferred is where Q is NH.

Preferred embodiments include where $R^1$ is H, OH, alkyl, alkoxy, halogen (preferably Cl, F or Br), $CR_3$, $NH_2$, NHR or NRR'. $R_3$ of $CR_3$ is $(halo)_3$, preferably $Cl_3$, $F_3$ or $Br_3$. R and R' of NHR and NRR' are independently alkyl. The term "independently," as used throughout, refers to independent selection of a group, but does not exclude the possibility that two groups are identical. For example, the alkyl group of R and R' of NRR' may be the same or different. Particularly preferred is where $R^1$ is alkyl, alkoxy or Cl.

Preferred embodiments include where $R^2$ is H, OH, alkyl, alkoxy, halogen (preferably Cl, F or Br), or $CR_3$. $R_3$ of $CR_3$ is $(halo)_3$, preferably $Cl_3$, $F_3$ or $Br_3$. Particularly preferred is where $R^2$ is Cl or Br.

Preferred embodiments include where $R^3$ is H, alkyl, alkoxy, halogen (preferably Cl), $CR_3$, $NH_2$, NHR or NRR'. $R_3$ of $CR_3$ is $(halo)_3$, preferably $Cl_3$. R and R' of NHR and NRR' are independently alkyl or acyl. Particularly preferred is where $R^3$ is alkyl or $NH_2$.

Preferred embodiments include where $R^4$, $R^5$ and $R^6$ are independently H, OH, alkyl, alkenyl, alkynyl, alkoxy, $(CH_2)_n$—OR, halogen (preferably Cl, F or Br), $CR_3$, acyl, heterocycle, $N^+(=O)O^-$, C≡N, $N_3$, SH, SR, $S(=O)_2R$, $NH_2$, NHR or NRR'. R of $(CH_2)_n$—OR is H or alkyl, and n is typically 1–10, with $CH_2$—OH and $(CH_2)_2$—OH preferred. $R_3$ of $CR_3$ is $(halo)_3$, preferably $Cl_3$, $F_3$ or $Br_3$. A preferred heterocycle is oxazol. A preferred acyl is phenone (so forms benzophenone when taken with the benzene ring to which it is attached) or ester, such as an amino acid ester derivative. R of SR and $S(=O)_2R$ is alkyl. R and R' of NHR and NRR' are independently alkyl. Particularly preferred is where $R^4$ or $R^5$ or $R^6$ is Cl, Br, $(CH_2)_2$—OH, $N^+(=O)O^-$, $C\equiv N$, or $C(=O)R$ the benzene ring to form a heterocycle. A preferred heterocycle is indazolyl, benzotriazolyl, indolyl, benzothiazolyl, benzimidazolyl or benzodioxolyl. Particularly preferred is where $R^4$ and $R^5$ (or $R^5$ and $R^6$) are taken together with the benzene ring to form indazole.

Particularly preferred compounds of the present invention are shown in Table 1 of Example 15 below, and physiologically acceptable salts thereof.

It may be advantageous for certain uses to enhance the solubility and/or bioavailability of one or more of the compounds of the present invention. This may be accomplished, for example, by the addition of one or more substituents to the compound. For example, the addition of hydrophilic groups, such as hydroxyl groups, may be advantageous. Other substituents for enhancing solubility and/or bioavailability include amino acids (e.g., polyglutamate or polylysine), di-peptides, polymers (e.g., PEG or POG), monocarboxylic acids (e.g., hemi-succinate), and esters. Any group that enhances solubility and/or bioavailability of a compound of the present invention may be used, provided that the group does not significantly impair the relevant biological property of the compound.

It may be advantageous for certain uses to prepare a compound (or physiologically acceptable salt thereof) as a "prodrug." As used herein, the term "compound" encompasses a prodrug form of the parent compound. "Prodrug" herein refers to a chemical substance that is converted into the parent compound in vivo. Prodrugs often are useful because, in some situations, they may be easier to administer than the parent compound. They may, for instance, be bioavailable by oral administration whereas the parent compound is not. The prodrug may also have improved solubility in pharmaceutical compositions over the parent compound. An example of a prodrug would be a parent compound of the present invention which is administered as an ester (the "prodrug") to facilitate transmittal across a cell membrane where water solubility is detrimental to mobility. The ester is then metabolically hydrolyzed to the carboxylic acid, the active entity, once inside the cell where water solubility is beneficial. Such a prodrug is generally inactive (or less active) until converted to the active form.

Pharmaceutical compositions of the compounds and the physiologically acceptable salts thereof are preferred embodiments of this invention. Pharmaceutical compositions of the compounds of the present invention (i.e., compounds and salts thereof as described above) may be manufactured by processes well known in the art; e.g., by means of conventional mixing, dissolving, granulating, dragee-making, levigating, emulsifying, encapsulating, entrapping or lyophilizing processes.

Pharmaceutical compositions may be formulated in a conventional manner using one or more physiologically acceptable carriers or diluents. Proper formulation is generally dependent upon the route of administration chosen. The pyridines of the present invention may be formulated such that the formulation comprises a single pyridine or a mixture of two or more pyridines described herein. Alternatively, one or more pyridines may be formulated with one or more other agents which are active for a general or specific disease, disorder or condition.

For injection, the compounds of the invention may be formulated as sterile aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with physiologically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be made with the use of a solid carrier or diluent, optionally grinding the resulting mixture, and processing the mixture of granules, after adding suitable auxiliaries, if desired, to obtain tablets or dragee cores. Suitable carriers or diluents are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the embodiments of the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoro-ethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical compositions for parenteral administration include sterile aqueous solutions of the active compounds in water soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation (see, for example, U.S. Pat. No. 5,702,717 for a biodegradable depot for the delivery of a drug). Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. The pharmaceutical compositions herein also may comprise suitable solid or gel phase carriers or diluents. Examples of such carriers or diluents include but are not limited to calcium carbonate, calcium phosphate, various sugars, starches, cellulose derivatives, gelatin, and polymers such as polyethylene glycols.

The compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartarate, maleate, succinate, etc. formed by the reaction of an amino group with the appropriate acid.

As noted above, LPAAT-β appears to play a role in various cellular pathways that have a connection to various diseases, disorders or conditions. The disclosure of the present invention shows unexpectedly that the pyridines set forth above inhibit the activity of LPAAT-β. This surprising inhibition is also specific for LPAAT-β, as the compounds tested showed weak to no inhibitory activity for LPAAT-α. In particular, none of the compounds tested had an $IC_{50}$ of less than 40 μM for LPAAT-α. In one use of the compounds of the present invention, the activity of LPAAT-β is reduced. The method comprises contacting LPAAT-β with a compound or salt thereof or composition of the present invention in an amount effective to reduce the LPAAT-β activity. The LPAAT-β to be contacted may reside in a cell-free preparation or in intact cells, including cells within an animal.

In the context of the present invention, the term "animal" refers to any animal, including humans and other primates, rodents (e.g., mice, rats, and guinea pigs), lagamorphs (e.g., rabbits), bovines (e.g., cattle), ovines (e.g., sheep), caprines (e.g., goats), porcines (e.g., swine), equines (e.g., horses), canines (e.g., dogs), felines (e.g., cats), domestic fowl (e.g., chickens, turkeys, ducks, geese, other gallinaceous birds, etc), as well as feral or wild animals, including such animals as ungulates (e.g., deer), bear, fish, lagamorphs, rodents, birds, etc. It is not intended that the term be limited to a particular age or sex. Thus, adult and newborn subjects, as well as fetuses, whether male or female, are encompassed by the term. A preferred animal within the present invention is a mammal, with humans particularly preferred.

In another use of the compounds of the present invention, the proliferation of a cell (in which the activity of LPAAT-β is required for the proliferation of the cell) is inhibited. The method comprises contacting the cell with a compound or salt thereof or composition of the present invention in an amount effective to inhibit the proliferation of the cell. The cell to be contacted may be in vitro or in vivo in an animal. An example of a cell whose proliferation it is desirable to inhibit is a tumor cell. However, there are other diseases, disorders and conditions with cell types other than tumor cells for which it may be desirable to inhibit proliferation of the cell. In the context of the present invention, the term "inhibiting" refers to both total inhibition and partial inhibition (i.e., the inhibition need not be 100%).

In another use of the compounds of the present invention, a cancer (in which LPAAT activity is associated) is treated. The method comprises administering to an animal in need, a compound or salt thereof or composition of the present invention in an amount effective to treat the cancer. In the context of the present invention, the term "treating a cancer" refers to any of a variety of positive effects from the treatment, including preventing the spread of a tumor, arresting tumor growth at a primary site, eradicating the tumor, relieving a symptom associated with the cancer, or prolonging the survival time of the animal treated. For example, as used herein, treating a cancer may have the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, (4) relieving to some extent (or, preferably, eliminating) one or more symptoms associated with the cancer, and/or (5) prolonging the survival time of the recipient. In addition, treatment further includes preventing tumor occurrence or recurrence. The method may further comprise inclusion of one or more other agents for treating a cancer. Alternatively, the method may be used in conjunction with one or more other cancer therapies, such as radiation, surgery or other chemotherapy.

Suitable routes of administration may include, without limitation, oral, rectal, transmucosal or intestinal administration or intramuscular, subcutaneous, intramedullary, intrathecal, direct intraventricular, intravenous, intraperitoneal or intranasal injections.

Alternately, one may administer the compound or composition in a local rather than systemic manner, for example, via injection of the compound or composition directly into a solid tumor, often in a depot or sustained release formulation.

Furthermore, one may administer the compound or composition in a targeted drug delivery system, for example, in a liposome coated with tumor-specific antibody. The liposomes will be targeted to and taken up selectively by the tumor.

Compounds and compositions suitable for use in the methods of the present invention are compounds and compositions wherein the active ingredients are contained in an amount effective to achieve its intended purpose. Determination of an effective amount is well within the capability of those skilled in the art, especially in light of the detailed disclosure provided herein.

For any compound or composition used in the methods of the invention, the effective amount or dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of LPAAT-β activity). Such information can be used to more accurately determine useful doses in humans.

Toxicity and therapeutic efficacy of the compounds described herein can be determined by standard pharmaceutical procedures in cell cultures or experimental animals for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (see, e.g., Fingl, et al., in "The Pharmacological Basis of Therapeutics," (1975), Chapter 1, pp. 1).

Dosage amount and interval may be adjusted individually to provide plasma levels of the active moiety which are sufficient to maintain LPAAT-β inhibitory effects, or minimal effective concentration (MEC). The MEC will vary for each compound but can be estimated from in vitro data; e.g., the concentration necessary to achieve 50–90% inhibition of LPAAT-β using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%. In cases of local administration or selective uptake, the effective local concentration of the drug may not be related to plasma concentration.

The amount of compound or composition administered will, of course, be dependent on the subject being treated, on the subject's weight, the severity of the affliction, the manner of administration and the judgment of the prescribing physician. An exemplary systemic daily dosage is about 5 to about 200 mg/kg of body weight. Normally, from about 10 to about 100 mg/kg of body weight of the compounds of the present invention, in one or more dosages per day, is effective to obtain the desired results. One of ordinary skill in the art can determine the optimal dosages and concentrations of the compounds of the preferred embodiments of the present invention with only routine experimentation.

The compounds of the present invention when used are substantially pure and preferably sterile. The phrase "substantially pure" encompasses compounds created by chemical synthesis or compounds substantially free of chemicals which may accompany the compounds in the natural state, as evidenced by thin layer chromatography (TLC) or high performance liquid chromatography (HPLC).

A compound or salt thereof of the present invention, or pharmaceutical composition of either, may be used to coat a medical device. A variety of medical devices, such as a stent, may be coated. The medical device may be composed of a bioadsorbable and biodegradable material. Due to the antiproliferative properties of the compounds of the present invention, a stent or other medical device that is coated with such a compound or salt thereof or pharmaceutical composition of either may be used for inhibiting the proliferation of a cell. The coated medical devices of the present invention may be used in a variety of ways. A preferred use is to inhibit the proliferation of tumor cells.

The following examples are offered by way of illustration and not by way of limitation.

EXAMPLES

Example 1

[2-Chloro-6-(5-chloro-2-methoxy-phenyl)-pyridin-4-yl]-p-tolyl-amine

To a solution of 4-amino-2,6-dichloropyridine (1.0 g, 6.1 mmol), 5-chloro-2-methoxy-phenylboronic acid (1.4 g, 7.3 mmol) and palladium acetate (137 mg, 0.61 mmol) in ethylene glycol dimethyl ether (50 ml), degassed with argon, was added a solution of cesium fluoride (3.8 g, 24.4 mmol) in water (10 ml) followed by triphenylphosphine (320 mg, 1.22 mmol). After stirring at 85° C. for 12 hours, the mixture was filtered through a pad of celite under suction. The filtrate was dried over sodium sulfate and purified by flash chromatography on silica gel eluting with ethyl acetate-hexane (1:4 followed by 2:5) to provide 2-chloro-6-(5-chloro-2-methoxy-phenyl)-pyridin-4-yl-amine (720 mg, 44% yield). $^1$H NMR (acetone-$d_6$) δ 3.91 (s, 3H, $CH_3$), 5.92 (s, 2H, $NH_2$), 6.60 (d, 1H, J=1.8 Hz, Ar), 7.14 (d, 1H, J=8.8 Hz, Ar), 7.33 (d, 1H, J=1.9 Hz, Ar), 7.37 (dd, 1H, J=8.8 Hz, J=2.8 Hz, Ar), 7.90 (d, 1H, J=2.8 Hz, Ar).

A mixture of 2-chloro-6-(5-chloro-2-methoxy-phenyl)-pyridin-4-yl-amine (715 mg, 2.65 mmol), p-tolylboronic acid (722 mg, 5.3 mmol), copper (II) acetate (962 mg, 5.3 mmol), triethylamine (1.5 ml, 10.6 mmol) and molecular sieves (4 angstrom) in dichloromethane (40 ml) was stirred under oxygen atmosphere for 60 hours. The mixture was filtered through a pad of celite under suction. The filtrate was purified by flash chromatography eluting with ethyl acetate-hexane (1:3 followed by 2:5) to provide the title compound (680 mg, 72% yield). $^1$H NMR (DMSO-$d_6$) δ 2.32 (s, 3H, $CH_3$), 3.91 (s, 3H, $CH_3$), 6.73 (d, 1H, J=1.9 Hz, Ar), 7.14 (d, 2H, J=8.4 Hz, Ar), 7.18 (d, 1H, J=8.9 Hz, Ar), 7.22 (d, 2H, J=8.2 Hz, Ar), 7.44–7.48 (m, 2H, Ar), 7.75 (d, 1H, J=2.8 Hz, Ar), 9.1 (s, 1H, NH).

Example 2

[4-Cloro-6-(5-chloro-2-methoxy-phenyl)-pyridin-2-yl]-p-tolyl-amine

To a mixture of 2,4,6-trichloropyridine (50 mg, 0.27 mmol), 5-chloro-2-methoxy-phenylboronic acid (54 mg, 0.28 mmol), cesium fluoride (100 mg, 0.66 mmol) in ethylene glycol dimethyl ether (10 ml), degassed with argon, was added tetrakis(triphenylphosphine)palladium(0) (30 mg, 0.026 mmol). The mixture was heated under reflux for 2 hours and filtered through a pad of celite under suction. The filtrate was concentrated under reduced pressure. The residue was purified by preparative thin layer chromatography eluting with ethyl acetate-hexane (1:9) to provide 2,4-dichloro-6-(5-chloro-2-methoxy-phenyl)-pyridine (25 mg, 32% yield). $^1$H NMR (acetone-$d_6$) δ 3.95 (s, 3H, CH$_3$), 7.24 (d, 1H, J=8.9 Hz, Ar), 7.49 (dd, 1H, J=8.9 Hz, J=2.8 Hz, Ar), 7.56 (d, 1H, J=2.8 Hz, Ar), 7.94 (d, 1H, J=2.8 Hz, Ar), 8.10 (d, 1H, J=1.6 Hz, Ar).

To a mixture of 2,4-dichloro-6-(5-chloro-2-methoxy-phenyl)-pyridine (25 mg, 0.087 mmol), p-tolylamine (10.2 mg, 0.1 mmol), sodium tert-butoxide (26 mg, 0.26 mmol), and tetrahydrofuran (15 ml), degassed with argon, was added palladium acetate (15 mg, 0.066 mmol) followed by 2,2'-bis(diphenylphosphino)-1,1'-binaphthyl (30 mg, 0.048 mmol). The mixture was stirred at 70° C. for 5 hours and filtered through a pad of celite under suction. The filtrate was concentrated under reduced pressure. The residue was purified by preparative thin layer chromatography eluting with ethyl acetate-hexane (1:9) to provide the title compound (6.6 mg, 21% yield). $^1$H NMR (acetone-$d_6$) δ 2.32 (s, 3H, CH$_3$), 3.95 (s, 3H, CH$_3$), 6.83–6.84 (m, 1H, Ar), 7.15 (d, 2H, J=8.2 Hz, Ar), 7.20 (d, 1H, J=8.9 Hz, Ar), 7.43 (dd, 1H, J=8.8 Hz, J=2.8 Hz, Ar), 7.46 (d, 1H, J=1.5 Hz, Ar), 7.57–7.60 (m, 2H, Ar), 8.10 (d, 1H, J=2.7 Hz, Ar), 8.43 (s, 1H, NH).

Example 3

6-(5-Chloro-2-methoxy-phenyl)-N*2*-p-tolyl-pyridine-2,4-diamine

A mixture of 2-chloro-6-(5-chloro-2-methoxy-phenyl)-pyridin-4-yl-amine, prepared in Example 1, (120 mg, 0.45 mmol) and p-tolylamine (1.0 g, 9.3 mmol) was heated at 190° C. for 45 minutes. After cooling to room temperature, the mixture was treated with hydrochloric acid (1 M, 50 ml). The mixture was extracted with ethyl acetate (50 ml). The organic extract was dried over magnesium sulfate and purified by flash chromatography on silica gel column eluting with ethyl acetate-hexane (1:4 followed by 1:1) to give the title compound (120 mg, 79% yield). $^1$H NMR (acetone-$d_6$) δ 2.27 (s, 3H, CH$_3$), 3.89 (s, 3H, CH$_3$), 5.30 (d, 2H, J=6.4 Hz, NH$_2$), 6.11 (d, 1H, J=1.7 Hz, Ar), 6.89 (d, 1H, J=1.7 Hz, Ar), 7.07 (d, 2H, J=8.3 Hz, Ar), 7.10 (d, 1H, J=8.8 Hz, Ar), 7.32 (dd, 1H, J=8.8 Hz, J=2.8 Hz, Ar), 7.51–7.54 (m, 2H, Ar), 7.68 (s, 1H, NH), 7.99 (d, 1H, J=2.8 Hz, Ar).

Example 4

6-(5-Chloro-2-methoxy-phenyl)-N*2*-(4-chlorophenyl)-pyridine-2,4-diamine

Following the method described in Example 3,2-chloro-6-(5-chloro-2-methoxy-phenyl)-pyridin-4-yl-amine and 4-chloro-phenylamine, provided the title compound (22% yield). $^1$H NMR (acetone-$d_6$) δ 3.90 (s, 3H, CH$_3$), 5.39 (s, 2H, NH$_2$), 6.90 (d, 1H, J=1.7 Hz, Ar), 7.12 (d, 1H, J=8.8 Hz, Ar), 7.24 (d, 2H, J=8.9 Hz, Ar), 7.34 (dd, 1H, J=8.8 Hz, J=2.8 Hz, Ar), 7.73 (d, 2H, J=8.9 Hz, Ar), 7.91 (d, 1H, J=2.8 Hz, Ar), 8.09 (s, 1H, NH).

Example 5

N-[6-(5-chloro-2-methoxy-phenyl)-4-p-tolylamino-pyridin-2-yl]-acetamide

A mixture of [2-chloro-6-(5-chloro-2-methoxy-phenyl)-pyridin-4-yl]-p-tolyl-amine (60 mg, 0.167 mmol) prepared according to Example 1, copper powder (100 mg, 1.54 mmol) and acetamide (2.0 g, 33.9 mmol) was heated at 180° C. for 3 hours. The mixture was purified by flash chromatography on silica gel eluting with ethyl acetate-hexane (1:1 followed by 3:2) to provide title compound (15 mg, 23% yield). $^1$H NMR (acetone-$d_6$) δ 2.19 (s, 3H, CH$_3$), 2.32 (s, 3H, CH$_3$), 3.91 (s, 3H, CH$_3$), 7.12 (d, 1H, J=8.8 Hz, Ar), 7.19–7.25 (m, 4H, Ar), 7.35 (dd, 1H, J=8.8 Hz, J=2.8 Hz, Ar), 7.47–7.48 (m, 1H, Ar), 7.86 (s, 1H, NH), 7.89 (d, 1H, J=2.8 Hz, Ar), 8.05 (s, 1H, NH).

Example 6

6-(5-Chloro-2-methoxy-phenyl)-N*4*-p-tolyl-pyridine-2,4-diamine

To a solution of N-[6-(5-chloro-2-methoxy-phenyl)-4-p-tolylamino-pyridin-2-yl]-acetamide (15 mg, 0.039) prepared according to Example 5 in ethanol (4 ml) was added hydrazine (0.01 ml). After heating under reflux for 3 hours, the mixture was concentrated under reduced pressure. The residue was treated with water (40 ml) and extracted with ethyl acetate (50 ml). The organic extract was dried over sodium sulfate, filtered, and concentrated under reduced pressure to give the title compound (6 mg, 45% yield). $^1$H NMR (acetone-$d_6$) δ 2.31 (s, 3H, CH$_3$), 3.90 (s, 3H, CH$_3$), 5.40 (s, 2H, NH$_2$), 6.16 (t, 1H, J=2.0 Hz, Ar), 7.04 (bs, 1H, Ar), 7.09 (t, 1H, J=8.8 Hz, Ar), 7.17 (bs, 4H, Ar), 7.32 (dd, 1H, J=8.8 Hz, J=2.8 Hz, Ar), 7.72 (s, 1H, NH), 7.93 (d, 1H, J=2.8 Hz, Ar).

Example 7

6-(5-Chloro-2-methoxy-phenyl)-N*4*-(4-chlorophenyl)-pyridine-2,4-diamine

Following the method described in Example 1,2-chloro-6-(5-chloro-2-methoxy-phenyl)-pyridin-4-yl-amine and 4-chloro-phenylboronic acid gave 2-chloro-6-(5-chloro-2-methoxy-phenyl)-pyridin-4-yl-(4-chloro-phenyl)-amine in 56% yield. $^1$H NMR (acetone-$d_6$) δ 3.92 (s, 3H, CH$_3$), 6.86 (d, 1H, J=8.9 Hz, Ar), 6.90 (t, 1H, J=1.9 Hz, Ar), 7.18 (d, 1H, J=8.9 Hz, Ar), 7.20 (d, 1H, J=8.9 Hz, Ar), 7.36 (d, 2H, J=8.9 Hz, Ar), 7.41 (dd, 1H, J=8.8 Hz, J=2.8 Hz, Ar), 7.46 (d, 2H, J=8.9 Hz, Ar), 7.72 (t, 1H, J=1.9 Hz, Ar), 7.95 (d, 1H, J=2.8 Hz, Ar).

Following the method described in Example 6,2-chloro-6-(5-chloro-2-methoxy-phenyl)-pyridin-4-yl-(4-chloro-phenyl)-amine provided the title compound (17% yield for 2 steps). $^1$H NMR (acetone-$d_6$) δ 3.90 (s, 3H, CH$_3$), 5.27 (s, 2H, NH$_2$), 6.22 (t, 1H, J=1.9 Hz, Ar), 7.09–7.12 (m, 2H, Ar), 7.26–7.36 (m, 5H, Ar), 7.86 (s, 1H, NH), 7.96 (d, 1H, J=2.8 Hz, Ar).

Example 8

4-(5-Chloro-2-methoxy-phenyl)-N-(4-chloro-phenyl)-pyridine-2,6-diamine

Chelidamic acid monohydrate (1.0 g, 5.0 mmol) was treated with pyridine (100 ml) and concentrated under vacuum and then treated with toluene (100 ml) and concentrated under vacuum. The residue was treated with dichloromethane (30 ml), N,N-dimethylformamide (0.3 ml) and a solution of oxalyl chloride in dichloromethane (2 M, 13.7 ml). After stirring for 1 hour, volatiles were evaporated under reduced pressure to give crude 4-chloro-pyridine-2,6-dicarbonyl dichloride.

To a mixture of crude 4-chloro-pyridine-2,6-dicarbonyl dichloride, dichloromethane (100 ml), and ethanol (5 ml), cooled in an ice bath, was added a solution of pyridine (6 ml) and ethanol (5 ml). The cooling bath was removed and the mixture was stirred for 5 hours. Volatiles were evaporated under reduced pressure. The residue was treated with a mixture of hydrochloric acid (1 M, 30 ml) and saturated aqueous sodium chloride solution (50 ml) and extracted with dichloromethane (200 ml). The organic extract was dried over magnesium sulfate and concentrated under reduced pressure. The residue was purified by flash chromatography on silica gel eluting with ethyl acetate-hexane (1:4 followed by 1:3) to provide 4-chloro-pyridine-2,6-dicarboxylic acid diethyl ester (800 mg, 62% yield). $^1$H NMR (DMSO-$d_6$) δ 1.36 (t, 6H, J=7.1 Hz CH$_3$), 3.33 (s, 3H, CH$_3$), 4.40 (q, 4H, J=7.1 Hz, CH$_2$), 8.31 (s, 2H, Ar).

To a solution of 4-chloro-pyridine-2,6-dicarboxylic acid diethyl ester (700 mg, 2.8 mmol), 5-chloro-2-methoxyphenylboronic acid (630 mg, 3.4 mmol), palladium acetate (105 mg, 0.47 mmol) in ethylene glycol dimethyl ether (50 ml), degassed with argon, was added a solution of sodium carbonate (868 mg, 8.2 mmol) in water (5 ml) followed by triphenylphosphine (220 mg, 0.84 mmol). The mixture was stirred at 80° C. for 3 hours and filtered through a pad of celite under suction. The filtrate was purified by flash chromatography on silica gel eluting with ethyl acetate-hexane (1:3 followed by 1:2) to give 4-(5-chloro-2-methoxy-phenyl)-pyridine-2,6-dicarboxylic acid diethyl ester (755 mg, 74% yield) as a white solid. $^1$H NMR (acetone-$d_6$) δ 1.42 (t, 6H, J=7.1 Hz CH$_3$), 3.92 (s, 3H, CH$_3$), 4.45 (q, 4H, J=7.1 Hz, CH$_2$), 7.27 (d, 1H, J=8.9 Hz, Ar), 7.52 (dd, 1H, J=8.8 Hz, J=2.7 Hz, Ar), 7.56 (d, 1H, J=2.7 Hz, Ar), 8.43 (s, 2H, Ar).

To a solution of 4-(5-chloro-2-methoxy-phenyl)-pyridine-2,6-dicarboxylic acid diethyl ester (700 mg, 2.7 mmol) in ethanol (40 ml) was added hydrazine (1.0 ml) and the mixture was heated under reflux for 3 hours. After cooling to 10° C., the solid was filtered and dried under vacuum to give 4-(5-chloro-2-methoxy-phenyl)-pyridine-2,6-dicarbonyl dihydrazide (618 mg, 100% yield). $^1$H NMR (DMSO-$d_6$) δ 3.92 (s, 3H, CH$_3$), 4.68 (s, 4H, NH$_2$), 7.24 (d, 1H, J=8.6 Hz, Ar), 7.53–7.56 (m, 2H, Ar), 8.20 (s, 2H, Ar), 10.72 (s, 2H, NH).

To a solution of 4-(5-chloro-2-methoxy-phenyl)-pyridine-2,6-dicarbonyl dihydrazide (600 mg, 2.61 mmol) in hydrochloric acid (0.5 M, 60 ml), cooled in an ice bath, was added a solution of sodium nitrite (1.7 g, 24.6 mmol) in water (5 ml). After stirring for 3 hours, the solid was filtered and dried under vacuum to give 4-(5-chloro-2-methoxy-phenyl)-pyridine-2,6-dicarbonyl diazide (600 mg, 91% yield) as a beige powder. $^1$H NMR (acetone-$d_6$) δ 3.94 (s, 3H, CH$_3$), 7.28 (d, 1H, J=8.9 Hz, Ar), 7.55 (dd, 1H, J=8.8 Hz, J=2.7 Hz, Ar), 7.62 (d, 1H, J=2.7 Hz, Ar), 8.54 (s, 2H, Ar).

To a solution of 4-(5-chloro-2-methoxy-phenyl)-pyridine-2,6-dicarbonyl diazide (310 mg, 1.23 mmol) in toluene (20 ml) was added tert-butanol (1 ml). The mixture was stirred at 100° C. for 30 minutes and volatiles were evaporated under reduced pressure. The residue was purified by flash chromatography on silica gel eluting with ethyl acetate-hexane (1:3) to provide [6-tert-butoxycarbonylamino-4-(5-chloro-2-methoxy-phenyl)-pyridin-2-yl]-carbamic acid tert-butyl ester (220 mg, 52% yield). $^1$H NMR (DMSO-$d_6$) δ 1.47 (s, 18H, CH$_3$), 3.79 (s, 3H, CH$_3$), 7.18 (d, 1H, J=8.9 Hz, Ar), 7.30 (d, 1H, J=2.6 Hz, Ar), 7.47–7.49 (m, 3H, Ar), 9.41 (s, 2H, NH).

To a solution of [6-tert-butoxycarbonylamino-4-(5-chloro-2-methoxy-phenyl)-pyridin-2-yl]-carbamic acid tert-butyl ester (220 mg, 0.49 mmol) in dichloromethane (8 ml) was added trifluoroacetic acid (6 ml). After stirring for 1 hour, volatiles were evaporated under reduced pressure. Treatment with toluene (15 ml) and evaporation of volatiles under reduced pressure provided 4-(5-chloro-2-methoxyphenyl)-pyridine-2,6-diamine trifluoroacetic acid salt (180 mg, 100% yield).

To a mixture of 4-(5-chloro-2-methoxy-phenyl)-pyridine-2,6-diamine trifluoroacetic acid salt (90 mg, 0.25 mmol), 4-chloro-phenylboronic acid (45 mg, 0.29 mmol), copper (II) acetate (218 mg, 1.2 mmol), 4A molecular sieves (5 g) in dichloromethane (20 ml) was added triethylamine (0.3 ml). The mixture was stirred under an oxygen atmosphere for 40 minutes and filtered through a pad of celite under suction. After evaporation of volatiles under reduced pressure, the residue was purified by flash chromatography on silica gel eluting with ethyl acetate-hexane (3:5 followed by 1:1 followed by 5:3) to provide the title compound (30 mg, 33% yield). $^1$H NMR (acetone-$d_6$) δ 3.84 (s, 3H, CH$_3$), 5.33 (d, 2H, J=8.8 Hz, NH$_2$), 6.16 (d, 1H, J=1.1 Hz, Ar), 6.27 (t, 1H, J=1.1 Hz, Ar), 7.12 (d, 1H, J=8.8 Hz, Ar), 7.23 (d, 2H, J=8.9 Hz, Ar), 7.30 (d, 1H, J=2.7 Hz, Ar), 7.36 (dd, 1H, J=8.8 Hz, J=2.7 Hz, Ar), 7.76–7.79 (m, 2H, Ar), 8.05 (s, 1H, NH).

Example 9

4-(5-Chloro-2-methoxy-phenyl)-4-p-tolyl-pyridine-2,6-diamine

Following the method described in Example 8,4-(5-chloro-2-methoxy-phenyl)-pyridine-2,6-diamine trifluoroacetic acid salt and p-tolyboronic acid provided the title compound (11% yield). $^1$H NMR (acetone-$d_6$) δ 2.26 (s, 3H, CH$_3$), 3.83 (s, 3H, CH$_3$), 5.24 (bs, 2H, NH$_2$), 6.10 (d, 1H, J=1.1 Hz, Ar), 6.26 (t, 1H, J=1.1 Hz, Ar), 7.06 (d, 2H, J=8.5 Hz, Ar), 7.08 (d, 1H, J=8.8 Hz, Ar), 7.29 (d, 1H, J=2.7 Hz, Ar), 7.35 (dd, 1H, J=9.0 Hz, J=3.3 Hz, Ar), 7.53–7.56 (m, 2H, Ar), 7.70 (s, 1H, NH).

Example 10

4-(5-Chloro-2-ethoxy-phenyl)-4-p-tolyl-pyridine-2,6-diamine

Following the method described in Example 8, (5-chloro-ethoxy-phenyl)-phenylboronic acid and 4-chloro-pyridine-2,6-dicarboxylic acid diethyl ester gave 4-(5-chloro-2-ethoxy-phenyl)-pyridine-2,6-diamine trifluoroacetic acid salt (4% yield for 5 steps).

Following the method described in Example 8,4-(5-chloro-2-ethoxy-phenyl)-pyridine-2,6-diamine trifluoroacetic acid salt and p-tolyboronic acid provided the title compound (17% yield). $^1$H NMR (acetone-$d_6$) δ1.35 (t, 3H, J=7.0 Hz, CH$_3$), 2.27 (s, 3H, CH$_3$), 4.08 (q, 2H, J=7.0 Hz, CH$_2$), 5.24 (bs, 2H, NH$_2$), 6.14 (d, 1H, J=1.0 Hz, Ar), 6.32 (t, 1H, J=0.9 Hz, Ar), 7.06–7.10 (m, 3H, Ar), 7.29–7.34 (m, 2H, Ar), 7.51–7.54 (m, 2H, Ar), 7.67 (s, 1H, NH).

Example 11

4-(5-Chloro-2-ethoxy-phenyl)-N-(4-chloro-phenyl)-pyridine-2,6-diamine

Following the method described in Example 8,4-(5-chloro-2-ethoxy-phenyl)-pyridine-2,6-diamine trifluoroacetic acid salt and 4-chloro-phenylboronic acid provided the title compound (30% yield). $^1$H NMR (acetone-$d_6$) δ1.35 (t, 3H, J=7.0 Hz, CH$_3$), 4.08 (q, 2H, J=7.0 Hz, CH$_2$), 5.32 (bs, 2H, NH$_2$), 6.21 (d, 1H, J=1.2 Hz, Ar), 6.32 (t, 1H, J=1.1 Hz, Ar), 7.09 (d, 2H, J=8.6 Hz, Ar), 7.23 (d, 2H, J=8.9 Hz, Ar), 7.31–7.78 (m, 2H, Ar), 8.04 (s, 1H, NH).

Example 12

4-[6-Amino-4-(5-chloro-2-ethoxy-phenyl)-pyridin-2-ylamino]-benzaldehyde

Following the method described in Example 8,4-(5-chloro-2-ethoxy-phenyl)-pyridine-2,6-diamine trifluoroacetic acid salt and 4-formyl-phenylboronic acid provided the title compound (22% yield). $^1$H NMR (acetone-$d_6$) δ1.36 (t, 3H, J=6.9 Hz, CH$_3$), 4.11 (q, 2H, J=7.0 Hz, CH$_2$), 5.51 (bs, 2H, NH$_2$), 6.33 (d, 1H, J=1.1 Hz, Ar), 6.44 (d, 1H, J=1.0 Hz, Ar), 7.12 (d, 1H, J=8.5 Hz, Ar), 7.31–7.37 (m, 2H, Ar), 7.78 (d, 2H, J=8.8 Hz, Ar), 7.88–7.97 (m, 2H, Ar), 8.57 (s, 1H, NH), 9.84 (s, 1H, CH).

Example 13

{4-[6-Amino-4-(5-chloro-2-ethoxy-phenyl)-pyridin-2-ylamino]-phenyl}-methanol To a solution of the title compound provided by Example 12 (25 mg, 0.068 mmol) in tetrahydofuran (5 ml) and methanol (10 ml) was added sodium borohydride (20 mg, 0.53 mmol). After stirring for 1.5 hours, the mixture was treated with water (10 ml) and hydrochloric acid (1 M, 0.6 ml). The mixture was concentrated to a volume of 8 ml and the solid was collected by filtration. The solid was treated with aqueous sodium carbonate solution (10%, 10 ml) and extracted with ethyl acetate (3×30 ml). The combined extracts were dried over sodium sulfate and concentrated under reduced pressure. The residue was purified by preparative thin layer chromatography eluting with methanol-dichloromethane (5:95) to give the title compound (10 mg, 39% yield). $^1$H NMR (acetone-$d_6$) δ1.36 (t, 3H, J=6.9 Hz, CH$_3$), 3.95 (bs, 1H, OH), 4.09 (q, 2H, J=7.0 Hz, CH$_2$), 4.56 (s, 2H, CH$_2$), 5.28 (bs, 2H, NH$_2$), 6.16 (d, 1H, J=1.1 Hz, Ar), 6.34 (d, 1H, J=1.1 Hz, Ar), 7.09 (d, 1H, J=8.5 Hz, Ar), 7.24 (d, 2H, J=8.8 Hz, Ar), 7.30–7.34 (m, 2H, Ar), 7.60–7.63 (m, 2H, Ar), 7.80 (s, 1H, NH).

Example 14

4-[6-Amino-4-(5-chloro-2-methoxy-phenyl)-pyridin-2-ylamino]-benzaldehyde

Following the method described in Example 8,4-(5-chloro-2-methoxy-phenyl)-pyridine-2,6-diamine trifluoroacetic acid salt and 4-formyl-phenylboronic acid provided the title compound (22% yield). $^1$H NMR (acetone-$d_6$) δ3.85 (s, CH$_3$), 5.51 (bs, 2H, NH$_2$), 6.27 (d, 1H, J=1.1 Hz, Ar), 6.38 (d, 1H, J=1.1 Hz, Ar), 7.14 (d, 1H, J=8.8 Hz, Ar), 7.32 (d, 1H, J=2.7 Hz, Ar), 7.38 (dd, 1H, J=8.8 Hz, J=2.7 Hz, Ar), 7.78 (d, 2H, J=8.7 Hz, Ar), 7.96 (d, 2H, J=8.7 Hz, Ar), 8.59 (s, 1H, NH), 9.84 (s, 1H, CH).

Example 15

LPAAT-β Assay

A. Production of Recombinant LPAAT-β for Assays

For the construction of Baculovirus expression vectors, the full-length human LPAAT-β cDNA was amplified by PCR from the DNA template pCE9.LPAAT-β (West et al., *DNA Cell Biol.* 16:691–701 (1997)) using the primers 5'-TGATATCCGA AGAAGATCTT ATGGAGCTGT GGC-CGTGTC-3' (olpb1F; SEQ ID NO:1) and 5'-CAG-GCTCTAG ACTACTGGGC CGGCTGCAC-3' (olpb1R; SEQ ID NO:2). The~870 bp fragment generated was reamplified by PCR using the primers 5'CCTACGTCG ACATG-GAACA AAAATTGATA TCCGAAGAAG ATC-3' (olpb2F; SEQ ID NO:3) and 5'-CAGGCTCTAG ACT-ACTGGGC CGGCTGCAC-3' (olpb1R; SEQ ID NO:2). The~890 bp fragment generated was then cleaved with Sal I and Xba I for insertion into pFastBac™ HTc vector (Life Technologies, Gaithersberg, Md.) between the Sal I and Xba I sites for the generation of the plasmid pFB.LPAAT-β. This plasmid was then transformed into *E. coli* DH10Bac™ (Life Technologies, Gaithersberg, Md.) for the generation of recombinant Bacmid DNA for transfection into HighFive (Invitrogen, San Diego, Calif.) or SF9 insect cells for the production of recombinant Baculovirus stocks using the protocol described in the Bac-to-Bac® Baculovirus Expression System (Life Technologies, Gaithersberg, Md.), a eukaryotic expression system for generating recombinant baculovirus through site-specific transposition in *E. coli*. Viral stocks harvested from the transfected cells can then be used to infect fresh insect cells for the subsequent expression of LPAAT-β fusion protein with a poly-histidine tag and a myc-epitope near its N-terminus. The membrane fraction from these Sf9 cells would be the source of LPAAT enzyme.

B. Preparation of Cell Membranes from Sf9 Cells

For the preparation of membranes from Sf9 Cells, all steps are performed on ice or at 4° C. Sf9 cell pellets (~10$^8$ cells) were thawed and resuspended in 1–2 ml of buffer A (20 mM Hepes, pH 7.5, 1 mM DTT, 1 mM EDTA, 20% w/v glycerol, 1 mM Benzamidine, 1 μg/ml soybean trypsin inhibitor (SBTI), 1 μg/ml pepstatin A) w/o DTT but with 1 mM Pefabloc. The cells were lysed by sonication using a Branson Sonifier at output=2, duty cycle=2, 10 pulses each at 10 s. with the tip of small sonicator probe submerged but not touching the walls. DTT was then added to 1 mM from a 1 M stock. The samples were centrifuged at 1500 rpm for 5 min. The low speed supernatant was saved and centrifuged (TLA 100.3 rotor, polycarbonate tubes, 2 ml/tube or 1.5 ml/tube minimum) at 100000×g for 1 hr. The high speed pellet was resuspend in Buffer A with a probe sonicator (10 pulses @ output #2 and duty cycle 20%) as a source of LPAAT enzyme.

C. Assay of LPAAT-β Activity

LPAAT-β catalyzes the transfer of an acyl group from a donor such as acyl-CoA to LPA. The transfer of the acyl group from acyl-CoA to LPA leads to the release of free CoA, which can be reacted with the thiol reagent, 5,5'-dithiobis(2-nitrobenzoic acid) (DTNB). The reaction between DTNB and the free sulfhydryl group from CoA generates a yellow-colored product, 3-carboxylato-4-nitrothiophenolate (CNP), that absorbs at 413 nm. LPAAT-β derived from Sf9 cell membrane overexpressing LPAAT-β were resuspended in HEPES saline buffer (20 mM HEPES pH 7.5, 150 mM NaCl), 1 mg/ml BSA and 72 μl aliquots were distributed into 96-well microtiter plates. 8 μl of compound of interest at 200 μM dissolved in 100% DMSO was added into each well. 20 μl of 1 mM 18:1-CoA and 1 mM sn-1-18:1 lysoPA was then added to each well to initiate the reaction and allowed to run at room temperature for 25 min. 100 μl of 1 mM DTNB in 100% ethanol was then added to each well to quench the reaction and for color development. The absorbance at 405 nm, measured using a spectrophotometer plate reader, is proportional to the activity of LPAAT-β in the sample. This colorimetric assay was used for the high throughput screening of LPAAT inhibitors. Compounds that showed >50% inhibition of the change in absorbance at 405 nm compared to control were selected for a secondary assay.

A secondary assay for LPAAT activity in cell extracts based on either the conversion of fluorescent NBD-LPA to NBD-PA (West, et al., *DNA Cell Biol.* 6:691–701, 1997) or [$^{14}$C]LPA to [$^{14}$C]PA using TLC analysis was used to screen compounds that showed >50% inhibition of LPAAT activity in the primary colorimetric assay. The radiometric assay was carried out in Sf9 cell membrane overexpressing LPAAT-β resuspended in HEPES-saline buffer, pH 7.5, 1 mg/ml BSA, 1 mM EDTA and 200 μM [$^{14}$C]18:1-CoA and 200 μM sn-1-18:1 lysoPA. The samples were incubated 7 min at 37° C., extracted into organic solvent ($CHCl_3/CH_3OH/HCl$ at 33/66/1), before loading onto TLC plates. A more detailed protocol for the radiometric assay is described below:

Specifically, this LPAAT assay is a modification of the acyltransferase assay published previously (Hollenback and Glomset, *Biochemistry* 37:363–376 (1999)).

1. The basic assay, in a total volume of 50 μl, employs a solution of substrates and the protein sample. Total assay volume, as well as the volume of each solution, can be changed to fit an experiment. In addition, other compounds, ex inhibitors and activators, can be included in the assay as well.

2. To prepare the solution of substrates:
   a. Stocks of Hepes (pH 7.5), NaCl, EDTA, BSA and acyl-CoA (from Serdery or Sigma) are mixed with water to make the appropriate concentration of each compound. This can be varied from assay-to-assay, but the final reaction mix is about 50 mM Hepes, 100 mM NaCl, 1 mM EDTA, 1 mg/ml BSA and 0–400 μM acyl-CoA.
   b. The lysoPA (from Avanti) is typically stored in chloroform and the $^{14}$C-labeled acyl-CoA (from Amersham) is typically stored in water/ethanol=1:1. Appropriate amounts of each solution are added the to a 12×75 mm borosilicate glass test tube and dry the solvent under $N_2$ or Ar. An appropriate volume of the solution prepared in 2a is added to the lysoPA and $^{14}$C-labeled acyl-CoA. The lipids are resuspend by sonication for 15 sec in a bath sonicator. The resulting suspension is then incubated (with occasional gentle vortexing) for about 10 minutes at room temp. The sn-1-16:0 lysoPA may require brief warming of the solvent to solubilize it. The concentration of lysoPA and $^{14}$C-labeled acyl-CoA can vary, but typically the final lysoPA concentration ranges between 0 and 400 μM and the $^{14}$C-labeled acyl-CoA specific activity ranges between 0.5 and 2 Ci/mol.

3. Protein sample: varies from experiment-to-experiment.

4. The assay is performed by mixing the components in 12×75 mm borosilicate glass test tubes (the order of addition does not matter unless indicated) and incubating at 37° C. for 5 to 10 minutes such that the assay within the linear range for time and protein.

5. The reaction is quenched by adding 1.3 ml of chloroform/methanol/HCl=48/51/0.7 and vortexing. 10 μl of carrier solution is then added (3 mg/ml each PA, ex. 16:0-18:1, and lysoPA, ex sn-1-18:1, in chloroform). Two phases are formed by adding 0.3 ml of water to each tube and vortexing.

6. The sample is centrifuged for 3 minutes at 1000×g, the upper (aqueous/methanol) phase is aspirated and the lower phase is dried under nitrogen.

7. Thin layer chromatography:
   a. The dried samples are resuspended in 50 μl of chloroform and a 15 μl aliquot is immediately spotted on an Analtech silica gel 60 HP-TLC plate (10×20 cm).
   b. Plates are developed in chloroform/methanol/acetic acid/water=85/12.5/12.5/3 (takes about 15 min) and dried.
   c. To be able to convert pixel volume (determined by the Storm phosphor imager, see step 8b) into cpm, cpm standard curve must be generated on the plate. $^{14}$C-labeled oleate dilutions in chloroform are made for this purpose. Four stocks (50 cpm/μl to 800 cpm/μl) are made and 2 μl of a different concentration are spotted in each corner of the plate (where previously there was no radioactivity).
   d. For quality control purposes, the plates are stained with primuline and scanned with the Storm (blue chemiluminescence mode).

The PA and lysoPA bands are easily detected in this system because of the carrier added in step 5. PA and lysoPA have respective Rf's of about 0.63 and 0.21.

8. Quantitating activity:
   a. The plates are then wrapped in saran wrap and exposed to a freshly blanked phosphor screen overnight (longer exposures can also be done to increase the signal).
   b. The screens are scanned (Phosphorimager mode), and LPAAT activity is determined by quantifying the pixels in the band comigrating with PA standard versus the standard curve generated from the cpm standards that were spotted in step 7c.

TABLE 1

| | | LPAAT-β cell-free assay | |
| Compound | | ($IC_{50}$, μM) | Compound Name |
| --- | --- | --- | --- |
| 1 | 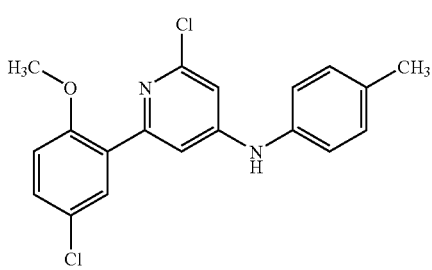 | 0.2 | [2-Chloro-6-(5-chloro-2-methoxy-phenyl)-pyridin-4-yl]-p-tolyl-amine |

TABLE 1-continued

| Compound | | LPAAT-β cell-free assay (IC$_{50}$, μM) | Compound Name |
|---|---|---|---|
| 2 | (structure) | >40 | [4-Chloro-6-(5-chloro-2-methoxy-phenyl)-pyridin-2-yl]-p-tolyl-amine |
| 3 | (structure) | 29 | 6-(5-Chloro-2-methoxy-phenyl)-N*2*-p-tolyl-pyridine-2,4-diamine |
| 4 | (structure) | 6.5 | 6-(5-Chloro-2-methoxy-phenyl)-N*2*-(4-chloro-phenyl)-pyridine-2,4-diamine |
| 5 | (structure) | 34 | N-[6-(5-chloro-2-methoxy-phenyl)-4-p-tolylamino-pyridin-2-yl]-acetamide |
| 6 | (structure) | 35 | 6-(5-Chloro-2-methoxy-phenyl)-N*4*-p-tolyl-pyridine-2,4-diamine |

TABLE 1-continued

| Compound | | LPAAT-β cell-free assay (IC$_{50}$, µM) | Compound Name |
|---|---|---|---|
| 7 | [structure] | 18 | 6-(5-Chloro-2-methoxy-phenyl)-N*4*-(4-chloro-phenyl)-pyridine-2,4-diamine |
| 8 | [structure] | 0.04 | 4-(5-Chloro-2-methoxy-phenyl)-N-(4-chloro-phenyl)-pyridine-2,6-diamine |
| 9 | [structure] | 0.24 | 4-(5-Chloro-2-methoxy-phenyl)-4-p-tolyl-pyridine-2,6-diamine |
| 10 | [structure] | 0.49 | 4-(5-Chloro-2-ethoxy-phenyl)-4-p-tolyl-pyridine-2,6-diamine |
| 11 | [structure] | 0.05 | 4-(5-Chloro-2-ethoxy-phenyl)-N-(4-chloro-phenyl)-pyridine-2,6-diamine |

TABLE 1-continued

| Compound | | LPAAT-β cell-free assay (IC$_{50}$, μM) | Compound Name |
|---|---|---|---|
| 12 | [structure] | 0.05 | 4-[6-Amino-4-(5-chloro-2-ethoxy-phenyl)-pyridin-2-ylamino]-benzaldehyde |
| 13 | [structure] | 0.1 | {4-[6-Amino-4-(5-chloro-2-ethoxy-phenyl)-pyridin-2-ylamino]-phenyl}-methanol |
| 14 | [structure] | 0.26 | 4-[6-Amino-4-(5-chloro-2-methoxy-phenyl)-pyridin-2-ylamino]-benzaldehyde |

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

The invention claimed is:

1. A compound or physiologically acceptable salt thereof, wherein the compound has the formula:

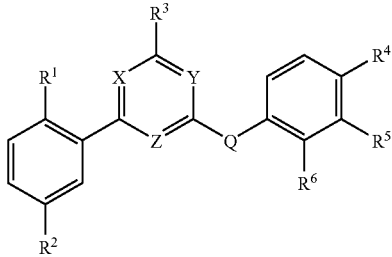

wherein:
- X is N, Y and Z are CH or CR where R is alkyl, alkoxy, Cl, Br, $NH_2$, NHR' or NR'R" where R' and R" independently are alkyl;
- Q is NR, RN—$(CH_2)_n$, $(CH_2)_n$—NR, S, S—$(CH_2)_n$ or $(CH_2)_n$—S, where n is 1–10 and R is H or alkyl;
- $R^1$ is H, OH, alkyl, alkoxy, Cl, F, Br, $CR_3$ where $R_3$ is $Cl_3$, $F_3$ or $Br_3$, $NH_2$, NHR or NRR' where R and R' independently are alkyl;
- $R^2$ is H, OH, alkyl, alkoxy, Cl, F, Br or $CR_3$ where $R_3$ is $Cl_3$, $F_3$ or $Br_3$;
- $R^3$ is H, alkyl, alkoxy, Cl, $CCl_3$, $NH_2$, NHR or NRR' where R and R' independently are alkyl or acyl;
- $R^4$, $R^5$, and $R^6$ are independently H, OH, alkyl, alkenyl, alkynyl, alkoxy, $(CH_2)_n$—OR where R is H or alkyl and n is 1–10, Cl, F, Br, $CR_3$ where $R_3$ is $Cl_3$, $F_3$ or $Br_3$, acyl, heterocycle wherein the heterocycle is oxazole, piperidine, piperazine, morpholine, pyrrole, furan, thiophene, imidazole, thiazole, pyrazole, pyridine or pyrimidine, $N^+(=O)O^-$, C≡N, $N_3$, SH, SR or $S(=O)_2$ R where R is alkyl, $NH_2$, NHR or NRR' where R and R' independently are alkyl, or $R^4$ and $R^5$ or $R^5$ and $R^6$ are taken together with the benzene ring to form a guinoline, isoquinoline, purine, carbazole or indazole.

2. The compound or salt thereof of claim 1 wherein Q of the compound or salt thereof is NH.

3. The compound or salt thereof of claim 1 wherein $R^4$ or $R^5$ of the compound or salt thereof is acyl.

4. The compound or salt thereof of claim 1 wherein $R^1$ of the compound or salt thereof is alkyl, alkoxy or Cl.

5. The compound or salt thereof of claim 1 wherein $R^2$ of the compound or salt thereof is Cl or Br.

6. The compound or salt thereof of claim 1 wherein $R^3$ of the compound or salt thereof is alkyl or $NH_2$.

7. The compound or salt thereof of 1 wherein $R^4$ or $R^5$ of the compound or salt thereof is alkyl, Cl, Br, $CF_3$, $CH_2$—OH, $(CH_2)_2$—OH, $N^+(=O)O^{31}$, C≡N, or C(=O)R wherein R is alkyl or alkoxy, or $R^4$ and $R^5$ are taken together with the benzene ring to form indazole.

8. The compound or salt thereof of claim 1 wherein the compound is [2-Chloro-6-(5-chloro-2-methoxy-phenyl)-pyridin-4-yl]-p-tolyl-amine, N-[6-(5-chloro-2-methoxy-phenyl)-4-p-tolylamino-pyridin-2-yl]-acetamide, 6-(5-Chloro-2-methoxy-phenyl)-N*4*-p-tolyl-pyridine-2,4-diamine, 6-(5-Chloro-2-methoxy-phenyl)-N*4*-(4-chloro-phenyl)-pyridine-2,4-diamine, or physiologically acceptable salts thereof.

9. A pharmaceutical composition comprising a compound or salt thereof according to claim 1 in combination with a pharmaceutically acceptable carrier or diluent.

10. The pharmaceutical composition of claim 9 wherein Q of the compound or salt thereof is NH.

11. The pharmaceutical composition of claim 9 wherein $R^4$ or $R^5$ of the compound or salt thereof is acyl.

12. The pharmaceutical composition of claim 9 wherein $R^1$ of the compound or salt thereof is alkyl, alkoxy or Cl.

13. The pharmaceutical composition of claim 9 wherein $R^2$ of the compound or salt thereof is Cl or Br.

14. The pharmaceutical composition of claim 9 wherein $R^3$ of the compound or salt thereof is alkyl or $NH_2$.

15. The pharmaceutical composition of claim 9 wherein $R^4$ or $R^5$ of the compound or salt thereof is alkyl, Cl, Br, $CF_3$, $CH_2$—OH, $(CH_2)_2$—OH, $N^+(=O)O^-$, C≡N, or C(=O)R wherein R is alkyl or alkoxy, or $R^4$ and $R^5$ are taken together with the benzene ring to form indazole.

16. The pharmaceutical composition of claim 9 wherein the compound is [2-Chloro-6-(5-chloro-2-methoxy-phenyl)-pyridin-4-yl]-p-tolyl-amine, N-[6-(5-chloro-2-methoxy-phenyl)-4-p-tolylamino-pyridin-2-yl]-acetamide, 6-(5-Chloro-2-methoxy-phenyl)-N*4*-p-tolyl-pyridine-2,4-diamine, 6-(5-Chloro-2-methoxy-phenyl)-N*4*-(4-choloro-phenyl)-pyridine-2,4-diamine, or physiologically acceptable salts thereof.

* * * * *